(12) United States Patent
Smith et al.

(10) Patent No.: US 10,893,834 B2
(45) Date of Patent: Jan. 19, 2021

(54) CHARGER FOR PRESSURE SENSING CATHETER

(71) Applicant: Laborie Medical Technologies Corp., Williston, VT (US)

(72) Inventors: Megan Melissa Smith, Nine Mile River (CA); Deepak Bhardwaj, Brampton (CA); Hooman Reza Zadeh Tabatabai, Richmond Hill (CA); Adrian G. Dacko, Mississauga (CA); Ing Han Goping, Oakvill (CA); Kristian Josef Olsen, Saratoga Springs, UT (US)

(73) Assignee: Laborie Medical Technologies Corp., Williston, VT (US)

( * ) Notice: Subject to any disclaimer, the term of this patent is extended or adjusted under 35 U.S.C. 154(b) by 0 days.

(21) Appl. No.: 16/046,061

(22) Filed: Jul. 26, 2018

(65) Prior Publication Data

US 2020/0029906 A1    Jan. 30, 2020

(51) Int. Cl.
*A61B 5/00*    (2006.01)
*A61B 5/20*    (2006.01)
(Continued)

(52) U.S. Cl.
CPC ............. *A61B 5/6853* (2013.01); *A61B 5/03* (2013.01); *A61B 5/037* (2013.01); *A61B 5/205* (2013.01);
(Continued)

(58) Field of Classification Search
None
See application file for complete search history.

(56) References Cited

U.S. PATENT DOCUMENTS

| 4,752,292 A | 6/1988 | Lopez et al. |
| 5,135,484 A | 8/1992 | Wright |

(Continued)

FOREIGN PATENT DOCUMENTS

| CN | 1859942 A | 11/2006 |
| EP | 774919 B1 | 11/2002 |

(Continued)

OTHER PUBLICATIONS

Smith et al., U.S. Appl. No. 16/045,895, filed Jul. 26, 2018, entitled "Pressure Catheter Connector," 45 pages.
(Continued)

*Primary Examiner* — Patrick Fernandes
*Assistant Examiner* — Benjamin S Melhus
(74) *Attorney, Agent, or Firm* — Fredrikson & Byron, P.A.

(57) ABSTRACT

A charger for charging a pressure sensing catheter is provided. The charger can include a plurality of charging ports for receiving a portion of the proximal section of the pressure sensing catheter. The charging port may include an engagement portion for engaging with the portion of the proximal section of the pressure sensing catheter such that when the engagement portion engages with the proximal section of the pressure sensing catheter, the engagement portion is fluidly coupled to the catheter lumen and the pressure transmission medium from the engagement portion is displaced from the engagement portion to charge the one or more balloons of the pressure sensing catheter. The charger can include a cover for covering the engagement portion. The charger can include flutes defined on a surface of each charging port to permit a predetermined volume of the pressure transmission medium to be displaced from each charging port.

19 Claims, 11 Drawing Sheets

(51) Int. Cl.
*A61B 5/03* (2006.01)
*A61M 25/10* (2013.01)
*A61M 39/10* (2006.01)

(52) U.S. Cl.
CPC .... *A61M 25/1018* (2013.01); *A61M 39/1011* (2013.01); *A61B 2562/227* (2013.01); *A61M 2039/1016* (2013.01); *A61M 2039/1022* (2013.01)

(56) References Cited

U.S. PATENT DOCUMENTS

| | | |
|---|---|---|
| 5,573,007 A | 11/1996 | Bobo |
| 5,776,116 A | 7/1998 | Lopez et al. |
| 5,795,325 A | 8/1998 | Valley et al. |
| 6,421,013 B1 | 7/2002 | Chung et al. |
| 6,649,829 B2 | 11/2003 | Garber et al. |
| 6,673,022 B1 | 1/2004 | Bobo et al. |
| 6,837,864 B1 | 1/2005 | Bertolero et al. |
| 7,352,771 B2 | 4/2008 | Garber |
| 7,926,856 B2 | 4/2011 | Smutney et al. |
| RE44,310 E | 6/2013 | Chadbourne et al. |
| 2004/0127813 A1 | 7/2004 | Schwamm |
| 2005/0064223 A1 | 3/2005 | Bavaro et al. |
| 2005/0187430 A1 | 8/2005 | Aundal et al. |
| 2005/0215119 A1 | 9/2005 | Kaneko |
| 2007/0073270 A1 | 3/2007 | Christensen |
| 2007/0252771 A1 | 11/2007 | Maezawa et al. |
| 2007/0273525 A1 | 11/2007 | Garber et al. |
| 2008/0030343 A1 | 2/2008 | Raybuck et al. |
| 2009/0009290 A1 | 1/2009 | Kneip et al. |
| 2009/0171278 A1 | 7/2009 | Hirszowicz et al. |
| 2009/0306539 A1 | 12/2009 | Woodruff et al. |
| 2010/0001516 A1 | 1/2010 | Pisula, Jr. et al. |
| 2010/0249663 A1 | 9/2010 | Nishtala |
| 2010/0249723 A1* | 9/2010 | Fangrow, Jr. ......... A61M 39/24 604/247 |
| 2010/0280451 A1 | 11/2010 | Teeslink et al. |
| 2011/0136550 A1 | 6/2011 | Maugars |
| 2011/0152841 A1 | 6/2011 | Nemoto |
| 2011/0210541 A1 | 9/2011 | Lewis et al. |
| 2013/0184612 A1 | 7/2013 | Quackenbush et al. |
| 2013/0268029 A1 | 10/2013 | Cauller et al. |
| 2013/0270820 A1 | 10/2013 | Py |
| 2014/0203077 A1 | 7/2014 | Gadh et al. |
| 2014/0266775 A1 | 9/2014 | Moon et al. |
| 2015/0130408 A1 | 5/2015 | Wei |
| 2015/0135502 A1 | 5/2015 | Rankin et al. |
| 2015/0250974 A1 | 9/2015 | Bobo, Sr. et al. |
| 2016/0029912 A1 | 2/2016 | Stimpson |
| 2016/0046130 A1 | 2/2016 | Burdge et al. |
| 2016/0089254 A1 | 3/2016 | Hopkinson et al. |
| 2016/0213228 A1 | 7/2016 | Rohl et al. |
| 2017/0021144 A1 | 1/2017 | Kanner et al. |
| 2017/0140330 A1 | 5/2017 | Rinzler et al. |
| 2017/0209682 A1 | 7/2017 | Shemesh |
| 2017/0258345 A1 | 9/2017 | Smith |
| 2017/0259035 A1 | 9/2017 | Smith et al. |

FOREIGN PATENT DOCUMENTS

| | | |
|---|---|---|
| EP | 1996851 B1 | 11/2011 |
| EP | 1799610 B1 | 11/2012 |
| EP | 1866611 B1 | 9/2014 |
| EP | 2837403 A1 | 2/2015 |
| EP | 3219353 A1 | 9/2017 |
| EP | 3332834 A1 | 6/2018 |
| WO | 2005032639 A1 | 4/2005 |
| WO | 2005107006 A1 | 11/2005 |
| WO | 2009055435 A1 | 4/2009 |

OTHER PUBLICATIONS

Smith et al., Design U.S. Appl. No. 29/657,875, filed Jul. 26, 2018, entitled "Pressure Catheter Connector," 11 pages.
International Patent Application No. PCT/US2019/043191, Invitation to Pay Additional Fees and Partial Search Report dated Dec. 11, 2019, 14 pages.
Yamashita, Noboru et al. "Preparation and characterization of gelatin sponge millispheres injectable through microcatheters", Medical Devices: Evidence and Research, 2009:2 19-25, 7 pgs.
English Abstract for Chinese Publication No. CN 1859942 A, published Nov. 8, 2006, 1 pgs.
International Patent Application No. PCT/US2020/015428, International Search Report and Written Opinion dated Jul. 7, 2020, 23 pages.

* cited by examiner

CHARGER FOR PRESSURE SENSING CATHETER

BACKGROUND

Pressure catheter devices can be used for the measurement and analysis of pressure within a body cavity. Such devices typically include an elongate catheter having at least one gas-filled pressure monitoring lumen extending longitudinally through the catheter. A gas-filled membrane (e.g., a balloon) can be formed on the outer surface of the catheter. The gas-filled membrane can be in fluid communication with the gas-filled pressure monitoring lumen. Changes in pressure against the gas-filled membrane may result in changes in pressure of the gas within the gas-filled pressure monitoring lumen. A pressure transducer connected to the proximal end of the gas-filled pressure monitoring lumen can sense and display or record the changes in pressure which can be communicated through the gas-filled pressure monitoring lumen of the catheter.

Some such pressure catheters may be connected by connectors to permit charging the gas-filled membrane. For instance, engagement of connectors may displace a volume of fluid and thereby charge the gas-filled membrane. Such catheters and connectors are described in commonly-assigned patent applications, U.S. 2017/0259035 A1 and U.S. 2017/0258345 A1, the entire contents of which is hereby incorporated by reference.

SUMMARY

In one aspect, a charger for charging a pressure sensing catheter, the pressure sensing catheter is provided. The catheter may include one or more balloons positioned in a distal section of the pressure sensing catheter that can be charged by a pressure transmission medium when the pressure sensing catheter is connected to the charger. The charger can include a plurality of charging ports for receiving a portion of the proximal section of the pressure sensing catheter. The charging port may include an engagement portion for engaging with the portion of the proximal section of the pressure sensing catheter such that when the engagement portion engages with the proximal section of the pressure sensing catheter, the engagement portion is fluidly coupled to the catheter lumen and the pressure transmission medium from the engagement portion is displaced from the engagement portion to charge the one or more balloons, and In optional embodiments, the charger can include a cover for covering the engagement portion. The cover can be movable between an open position and a closed position, wherein, in the closed position, the cover fluidly seals the engagement portion. The cover can be movable to the open position to permit engagement of the portion of the proximal section with the engagement portion.

In another aspect, the charger can include a plurality of flutes defined on a surface of each charging port to permit a predetermined volume of the pressure transmission medium to be displaced from each charging port when the portion of each charging port engages with the portion of the proximal section of the corresponding pressure sensing catheter.

Embodiments of the present disclosure also include one or more of the following numbered embodiments:

1. A charger for charging a pressure sensing catheter, the pressure sensing catheter comprising a catheter lumen extending from a distal section to a proximal section of the pressure sensing catheter, one or more balloons positioned in the distal section of the pressure sensing catheter, the one or more balloons being charged by a pressure transmission medium when the pressure sensing catheter is connected to the charger, the charger comprising: a charger housing;
   a plurality of charging ports, each charging port configured to receive a portion of the proximal section of the pressure sensing catheter, each charging port comprising:
   an engagement portion for engaging with the portion of the proximal section of the pressure sensing catheter, the engagement portion having the pressure transmission medium therewithin such that when the engagement portion engages with the proximal section of the pressure sensing catheter, the engagement portion is fluidly coupled to the catheter lumen and the pressure transmission medium is displaced from the engagement portion to charge the one or more balloons, and
   a cover for covering the engagement portion, the cover being movable between an open position and a closed position, wherein, in the closed position, the cover fluidly seals the engagement portion, and the cover being movable to the open position to permit engagement of the portion of the proximal section with the engagement portion.
2. The charger of embodiment 1, wherein the cover is rotatable relative to the engagement portion about a rotational axis, the rotational axis being non-parallel with a central axis of the engagement portion.
3. The charger of embodiment 1 or 2, wherein the rotational axis is generally perpendicular to the central axis of the engagement portion.
4. The charger of embodiment 2 or any previous embodiment, wherein the cover comprises a cover base pivotably coupled to the charger housing to rotate the cover between the open position and the closed position.
5. The charger of embodiment 4 or any previous embodiment, wherein the cover base comprises a generally planar surface, the generally planar surface of the cover base being generally coplanar with a generally planar surface of the charger housing when the cover is in the closed position.
6. The charger of embodiment 5 or any previous embodiment, wherein the generally planar surface of the cover base being generally non-coplanar with the generally planar surface of the charger housing when the cover is in the open position.
7. The charger of embodiment 6 or any previous embodiment, wherein the generally planar surface of the cover base forms an angle with the generally planar surface of the charger housing when the cover is in the open position.
8. The charger of embodiment 7 or any previous embodiment, wherein the charger door is configured to remain in an open position when rotated away from the charging port beyond a first rotational position.
9. The charger of embodiment 8 or any previous embodiment, wherein the charger housing comprising a charger housing angled surface, the cover base resting against the charger housing angled surface when in the open position so as to maintain the cover in the open position and to provide clearance for insertion of the connector.
10. The charger of embodiment 4 or any previous embodiment, wherein, the cover base terminates in a clip, the clip having a protrusion, the charger housing having a charger housing end surface, the charger housing end surface forming an angle with the charger housing angled surface, the protrusion resting against the charger housing end surface when the cover is in the open position to inhibit inadvertent closure of the cover.
11. The charger of embodiment 4 or any previous embodiment, wherein the cover being movable between the open position and the closed position by manually applying a force on the cover.
12. The charger of embodiment 4 or any previous embodiment, wherein the cover comprises a cover plug extending from the cover base, the cover plug having an interference fit with the engagement portion to maintain the cover is in the closed position.
13. The charger of embodiment 12 or any previous embodiment, wherein the cover plug is resilient relative to the cover base, the cover plug fluidly sealing the engagement portion when received therewithin.
14. The charger of embodiment 13 or any previous embodiment, wherein the cover plug comprises a resilient material having a Shore A durometer hardness of between about 50 and about 95.
15. The charger of embodiment 1 or any previous embodiment, wherein each cover is removably connectable to each charging port.
16. The charger of embodiment 1 or any previous embodiment, wherein in the closed position, each cover can engage by a snap-fit with each charging port.
17. A charger for charging one or more pressure sensing catheters, each pressure sensing catheter comprising a catheter lumen extending from a distal section to a proximal section thereof, one or more balloons positioned in the distal section of each pressure sensing catheter, the one or more balloons being charged by a pressure transmission medium when each pressure sensing catheter is connected to the charger, the charger comprising:
   a charger housing;
   a plurality of charging ports, each charging port configured to receive a portion of the proximal section of a corresponding pressure sensing catheter, each charging port having a central axis, each charging port having the pressure transmission medium therewithin such that when the proximal section of the corresponding pressure sensing catheter engages with a portion of each charging port, the portion of each charging port is fluidly coupled to the catheter lumen and the pressure transmission medium is displaced from the portion of each charging port to charge one or more balloons of the corresponding pressure sensing catheter; and
   a plurality of flutes defined on a surface of each charging port, the plurality of flutes permitting a predetermined volume of the pressure transmission medium to be displaced from each charging port when the portion of each charging port engages with the portion of the proximal section of the corresponding pressure sensing catheter.
18. The charger of embodiment 17 or any previous embodiment, wherein each charging port has an engagement portion for receiving the portion of the proximal section of the corresponding pressure sensing catheter.
19. The charger of embodiment 18 or any previous embodiment, wherein each flute of the plurality of flutes is defined on an interior surface of each charging port.
20. The charger of embodiment 19 or any previous embodiment, wherein each flute of the plurality of flutes is defined on the interior surface of each charging port at evenly spaced intervals.
21. The charger of embodiment 17 or any previous embodiment, further comprising a plurality of pressure transducers, each pressure transducer being positioned near an end of each charging port.
22. The charger of embodiment 21 or any previous embodiment, wherein each transducer is oriented to be generally perpendicular to the central axis.
23. A pressure sensing system, comprising:
   a pressure sensing catheter, comprising:
   a proximal section and a distal section opposite to the proximal section,
   a catheter lumen extending from the proximal section to the distal section,
   one or more balloons, at least one of the one or more balloons being fluidly coupled to the catheter lumen and positioned at the distal section, the one or more balloons being charged by a pressure transmission medium, and
   a connector positioned at the proximal section of the pressure sensing catheter, the connector comprising:
   a body having a lumen fluidly connectable to the catheter lumen of the pressure sensing catheter for transmitting the pressure transmission medium;
a first engagement portion attached to the body, and
   a handle attached to the body, the handle being depressable relative to the body, the handle comprising a first end and a second end opposite to the first end, the first end having a tab terminating in an end surface; and
   a charger, comprising:
   a charger housing comprising an engagement surface;
   a plurality of charging ports, each charging port having:
   a central axis,
   a second engagement portion, the second engagement portion being engageable with the first engagement portion, wherein engagement of the first engagement portion with the second engagement portion fluidly couples the catheter lumen and displaces the pressure transmission medium present in the second engagement portion to charge the one or more balloons,
   the end surface of the tab being engageable with the engagement surface of the charger housing when the first engagement portion engages with the second engagement portion, and
   when the second end of the handle is depressed, the second end of the handle applies a disengagement torque on the first end, thereby permitting disengagement of the first engagement portion with the second engagement portion thereby disengaging the pressure sensing catheter and the charger.
24. The pressure sensing system of embodiment 23 or any previous embodiment, wherein the engagement surface is exterior to the second engagement portion.
25. The pressure sensing system of embodiment 24 or any previous embodiment, wherein the engagement surface protrudes laterally outwardly relative to the central axis so as to form a lip, the end surface of the tab abutting the lip of the engagement surface.
26. The pressure sensing system of embodiment 25 or any previous embodiment, wherein, when the second end of the handle is depressed, the disengagement torque releases the abutment between the end surface of the tab and the lip of the engagement surface.

27. The pressure sensing system of embodiment 23 or any previous embodiment, wherein the first engagement portion has a proximal end portion, and the second engagement portion has a proximal end portion, the proximal end portion of the first engagement portion abutting the proximal end portion of the second engagement portion when the end surface of the tab engages with the engagement surface.
28. The pressure sensing system of embodiment 23 or any previous embodiment, wherein sealing engagement between the first engagement portion and the second engagement portion displaces a first volume of pressure transmission medium present in the charging port into the lumen of the connector, the first volume being generally less than a second volume of pressure transmission medium present in the charging port prior to engagement between the first engagement portion and the second engagement portion, a difference between the first volume and the second volume being about equal to a dead space.
29. The pressure sensing system of embodiment 28 or any previous embodiment, wherein
the charger comprises a plurality of pressure transducers positioned against a proximal aperture of each charging port, each pressure transducer comprising
a proximal end surface, and
the first engagement portion of the connector terminating in a proximal end surface, the proximal end surface of the connector being spaced apart from the proximal end surface of the pressure transducer by a portion of the dead space.
30. The pressure sensing system of embodiment 29 or any previous embodiment, wherein, the proximity of the proximal end surface of the connector and the proximal end surface of the pressure transducer permits direct fluid communication between the one or more balloons and the pressure transducer, thereby permitting the pressure transducer to measure pressure at a rate so as to capture anatomical pressure variations having a characteristic frequency of between about 1 Hz and about 50 Hz.
31. The pressure sensing system of embodiment 30 or any previous embodiment, wherein a ratio of the dead space to the first volume is less than about 1:2.5.
32. The charger of embodiment 1 or any previous embodiment, further comprising a plurality of pressure transducers positioned against a proximal end of each charging port, each pressure transducer configured to fluidly isolate a corresponding charging port from an interior of the charger having electrical components, such that fluid entering into the charging port is prevented from entering the electrical components.

The details of one or more examples are set forth in the accompanying drawings and the description below. Other features, objects, and advantages will be apparent from the description and drawings, and from the claims.

DETAILED DESCRIPTION

For purposes of illustrating the various aspects of the methods and systems claimed herein, the discussion below will be directed to describing exemplary embodiments used in anatomical pressure sensing catheter associated connectors, charger (which includes one or more charging ports) and a measurement system. The term "charger," as used herein, may also include one or more of the following: a measurement system which includes transducers, associated electrical circuitry and the like. The elements and principles discussed herein are applicable to applications such as urodynamic, esophageal, anorectal manometry, and the like. Further, the exemplary embodiments described herein are contemplated for use with any type of catheter 10 wherein measurement of pressure within the body of a patient is desired. Discussion of methods and systems herein can be interchangeable with respect to specific aspects. In other words, specific discussion of one method or system (or components thereof) herein is equally applicable to other aspects as they relate to the system or method, and vice versa.

Figure 1:
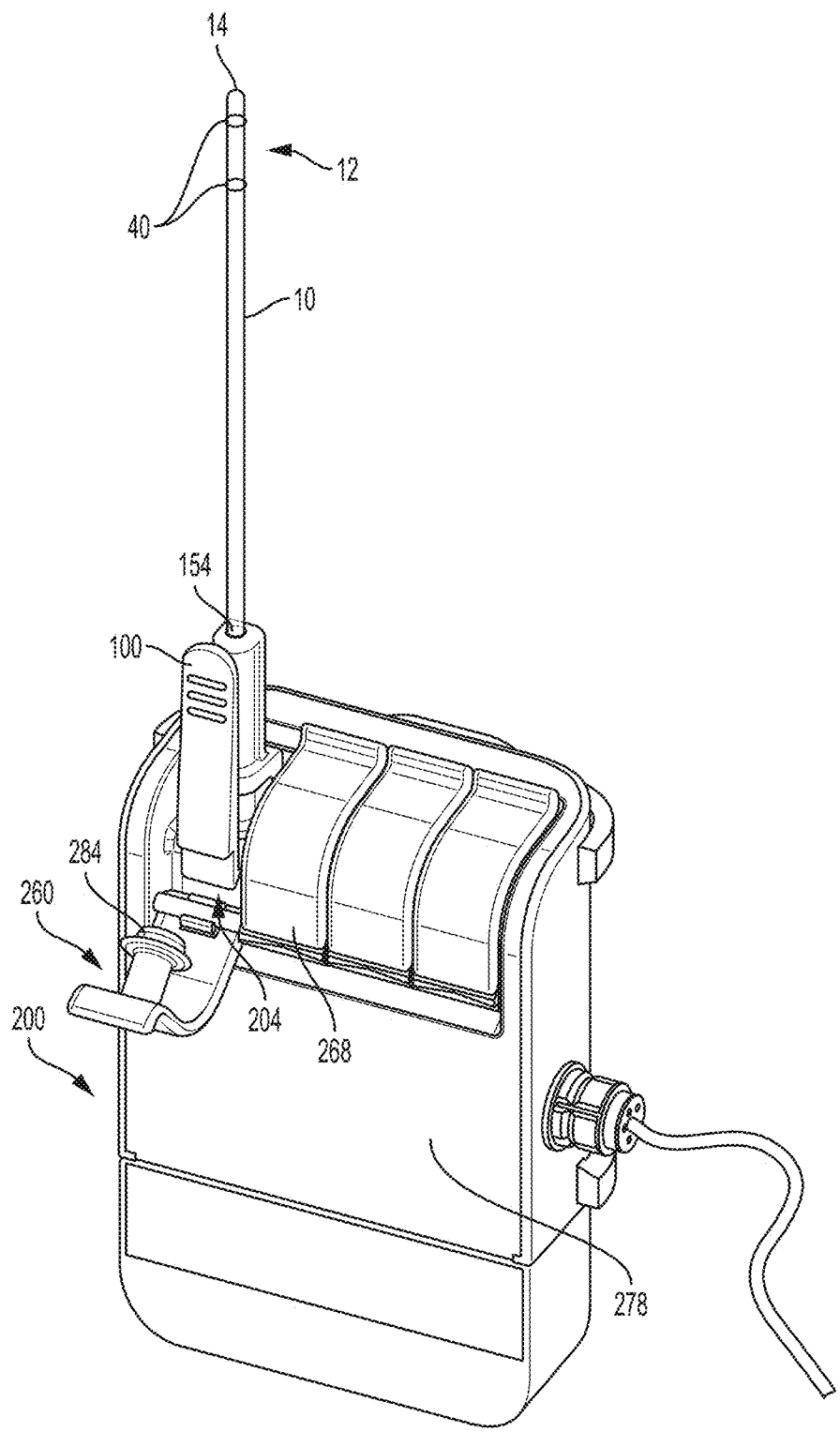
FIG. 1 is a perspective view of an anatomical pressure sensing system according to an embodiment.

FIG. 1 is a perspective view of an anatomical pressure sensing system according to an embodiment. The pressure sensing system may include a catheter 10, a catheter connector 100 and a charger 200, which, as noted above, can refer to one or more of the charging ports, but can also include, measurement system, transducers and the like. Aspects of the present disclosure relate to various features of one or more of catheter 10, catheter connector 100 and/or charger 200.

Figure 2:
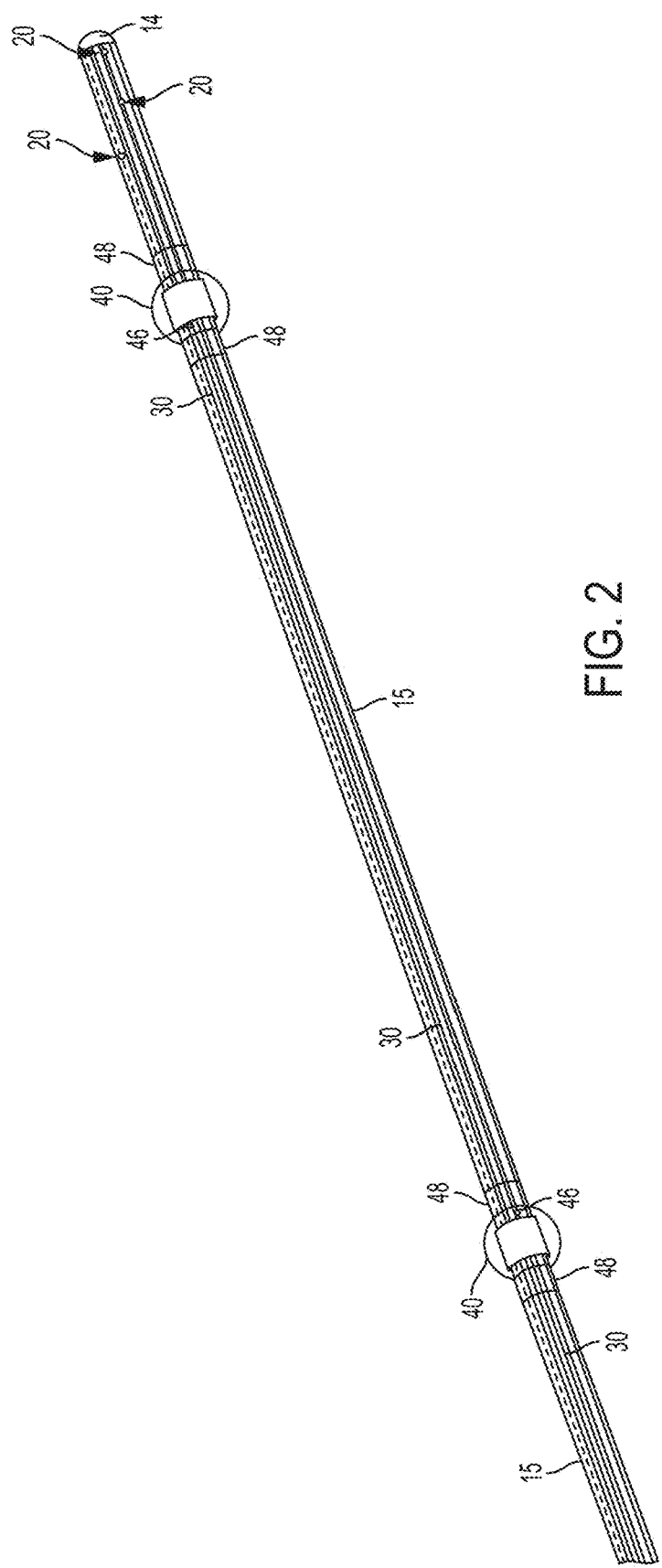
FIG. 2 is an enlarged view of a distal portion of a catheter according an embodiment.

FIG. 2 is an enlarged perspective view of a catheter 10 in accordance with a non-limiting exemplary embodiment. The pressure sensing catheter 10 comprises a proximal section and a distal section 12. The distal section 12 of the catheter 10 comprises a soft, pliant tip 14 which facilitates insertion of the catheter 10 into the patient. The soft tip 14 may optionally be formed of a material which is pliant enough to deflect as the tip 14 encounters a resistive force, such as from a tissue. A low durometer plastic or elastomer, such as polyvinyl chloride (PVC) or a polyurethane, is suitable though other materials having a suitable rigidity/pliancy and/or optionally deemed safe for use inside the cavity or vessel of a subject or patient can be used.

With continued reference to FIG. 2, the tip 14 is formed from an elongated hollow tube 15 which extends from the tip 14 at its distal section 12 to a connector 100 on its proximal section. The hollow tube 15 is formed of flexible, biocompatible material, such as PVC or a polyolefin, with sufficient properties, such as wall thickness, to resist collapse under normal conditions, and sized in length to extend from within a cavity (e.g., urinary tract) of a patient to outside the body of the patient.

As seen from FIG. 2, one or more flaccid, pressure-compliant members (e.g., a medical grade balloon or bladder used in medical applications) 40 are located on a distal section 12 of the catheter 10. The balloons 40 are configured to receive a predetermined volume of a pressure transmission medium (e.g., air or other fluids) to resist induced pressure forces acting externally on the balloon 40. The induced pressure forces are transmitted through the balloon 40 and down a monitor lumen 30 within the catheter 10.

In certain embodiments, with reference to FIG. 2, the balloon 40 may be formed as a substantially circular body disposed about and/or attached to an opening 46 of a secondary (or monitor) lumen 30 and/or heat-sealed at the ends 48 of the balloon 40. While a circular shape is illustrated, other shapes may be used. A pressure transmission medium (e.g., air) may occupy the interior of the secondary lumen 30. In such cases, fluid may be at atmospheric pressure prior to use of the catheter 10. The secondary lumen 30 and the balloon 40 attached to the secondary lumen 30 (including any portion of the secondary lumen 30 that extends within the connector 100) may, therefore, form or define a fluid column which extends from inside the connector 100 to near the tip 14 of the catheter 10. When the catheter 10 attached to connector 100 is engaged with a charging port 204 of the charger 200, as explained further below, the balloon becomes at least partially filled, or "charged," with an additional quantity of fluid (e.g., present in the charger 200). The additional fluid charged into the fluid column partially fills the balloon 40 to a selected volume.

In certain embodiments, the balloon 40 can be in a substantially deflated state prior to, during and/or shortly after insertion of the distal section 12 of the catheter 10 inside a body cavity. With charging, the balloon 40 becomes at least partially filled with the pressure transmission medium (e.g., air). Thus, depending on the quantity of the pressure transmission medium present in the balloon 40 prior to charging, the balloon 40 may be filled between about 40% and about 70% of its capacity following charging. In optional embodiments, balloon 40 may not be overfilled so as to not introduce the structure of the balloon 40 into the signal. In some such cases, the flaccidity of the partially-filled working volume of balloon 40 can reduce aberrant effects in pressure detection due to temperature changes (e.g., from Charles's Law), or other undesirable effects which may introduce signal artifacts due to the balloon 40 wall internal forces, or external balloon 40 compression from debris, or other undesirable effects.

According to certain aspects of the present disclosure, the low durometer material of the balloon 40 may allow the surface of the balloon 40 to deform with an increase in pressure. Therefore, a change in body cavity pressure may deform the balloon 40 and, in turn, be communicated (via the fluid column within the balloon 40 and the monitor lumen 30) to a pressure transducer 222 (to be described further below), which can in turn be converted to an electrical signal. In one embodiment, changes in a range of about (0, 200) mmHg of pressure can be measured.

In some examples, each balloon 40 may have its own, separate, monitor lumen 30. Accordingly, in some examples, a fluid column can be defined by pressure transmission medium (e.g., air) within the monitor lumen 30 (including the monitor lumen 30 within the connector 100) and the balloon 40. The fluid columns (for instance, defined in the monitor lumen 30 and internal balloon 40 volume) of each balloon 40 may not be in fluid communication with one another. Rather, balloons 40 can be independently charged by connection of respective connector 100 assemblies (such as those described elsewhere herein).

Figure 3:
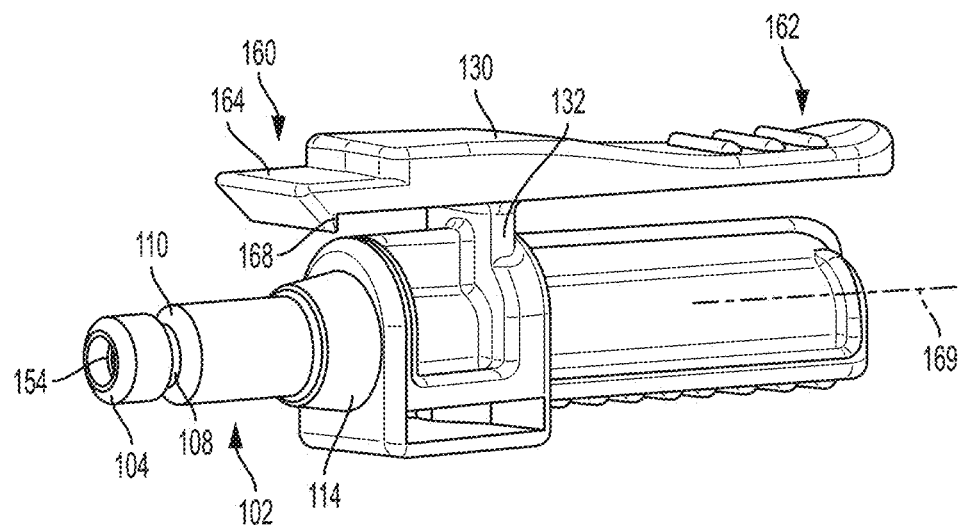
FIG. 3 is a perspective view of a catheter connector according to an embodiment.
Figure 4:
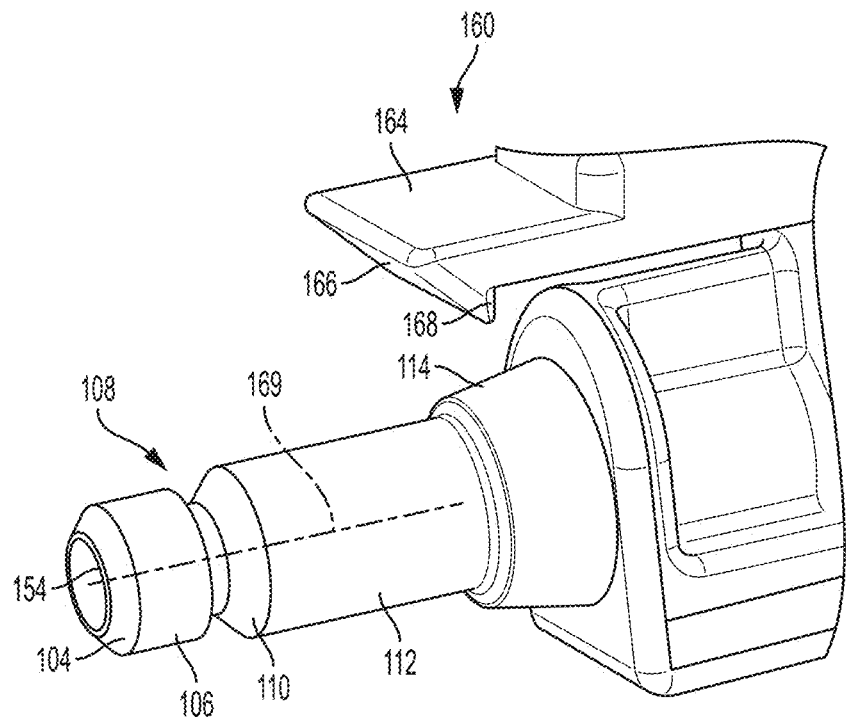
FIG. 4 is an enlarged perspective view of the catheter connector of FIG. 3.

FIGS. 3 and 4 illustrate details of a representative connector 100. The connector 100 can, in some examples, be a male connector and can be received within a charging port 204 of a charger 200. While the illustrated embodiments show the connector provided on the catheter side, and the charging port provided on the charger side, it should be understood that their respective functionalities can be reversed, and specific components disclosed as being located on the catheter connector can be located on the charger and vice versa. The connector 100 can include a central lumen 154, into which the catheter 10 may be inserted.

In some advantageous examples, with continued reference to FIGS. 3 and 4, the connector 100 can have a first engagement portion 102 for engaging with a corresponding charger engagement portion of a charging port 204 (described further below). Engagement of the first engagement portion 102 with the charger engagement portion displaces the pressure transmission medium present in the charger engagement portion to charge one or more balloons 40.

The first engagement portion 102 can have a variable cross-sectional area to align with various portions of a charging port 204 of a charger 200. In the illustrated embodiment, the first engagement portion 102 can include a proximal end portion 104, a proximal abutment portion 106, a seal groove 108, a ramp portion 110, a connecting portion 112, and a distal abutment portion 114. One or more of such portions can have a variable cross-sectional area.

As seen in FIG. 4, in one example, the proximal end portion 104 can have a cross-sectional area less than a cross-sectional area of the proximal abutment portion 106. The seal groove 108 can have a cross-sectional area less than the cross-sectional area of the proximal abutment portion 106. A connecting portion 112 can have a cross-sectional area greater than the cross-sectional area of the seal groove 108. Accordingly the ramp portion 110 can have a gradually variable cross-sectional area, transitioning from the cross-sectional area of the seal groove 108 to the cross-sectional area of the connecting portion 112. The distal abutment portion 114 can have a cross-sectional area greater than the cross-sectional area of the connecting portion 112. Further, the distal abutment portion 114 may either have a constant cross-sectional area over its length, or a variable (e.g., gradually variable) cross-sectional area over its length.

Figure 5:
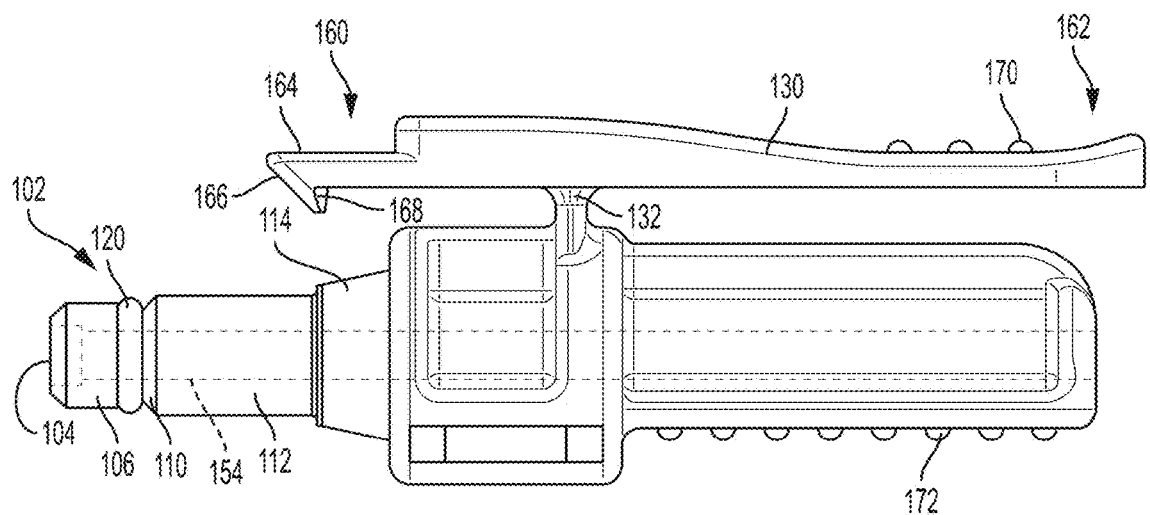
FIG. 5 is a side view of the catheter connector of FIG. 3 illustrating a seal positioned prior to insertion.
Figure 6:
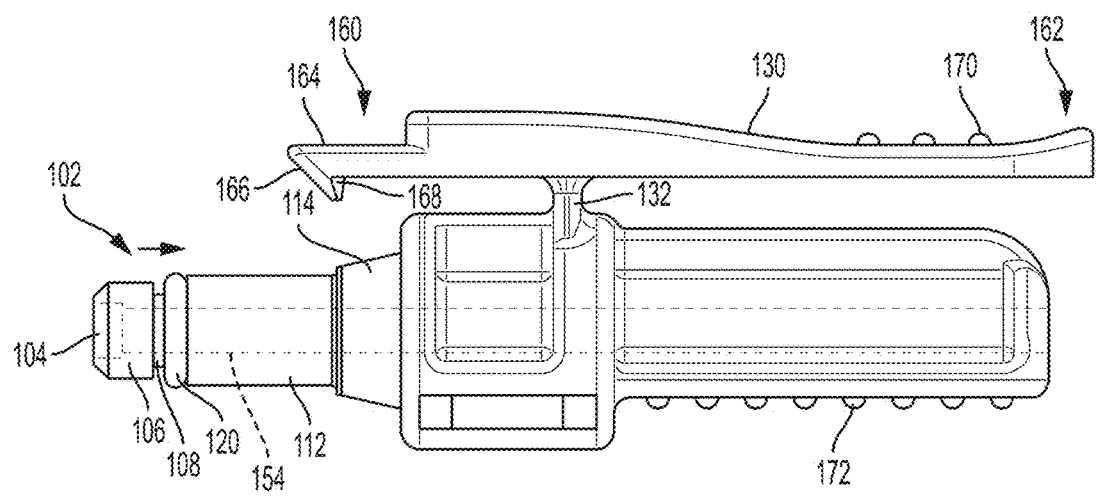
FIG. 6 is a side view of the catheter connector of FIG. 3 illustrating a seal positioned after insertion.

In some such examples, as illustrated in FIGS. 5 and 6, a resilient member 120 can be positioned between the proximal end portion 104 and the ramp portion 110, for instance, in the seal groove 108. The cross-sectional area of the ramp portion 110 transitions from the cross-sectional area of the seal groove 108 to the cross-sectional area of the connecting portion 112. The resilient member 120 can, in some such cases, ride on the ramp portion 110 during engagement of the first engagement portion 102 (with a corresponding charging port 204) to a form a fluid tight seal. The resilient member 120 can optionally be an O-ring to permit a fluid tight connection and optionally control the charge volume precisely.

Referring again to FIGS. 3-6, in certain embodiments, the connector 100 can include a handle 130 attached to its body. The handle 130 can facilitate engagement and/or disengagement of the connector 100 with a corresponding charging port 204 in a controlled fashion, further providing the operator with the possibility of controlling the charge volume more precisely. The handle 130 can be rigidly attached to the body at a handle attachment portion 132. In the illustrated embodiment, the handle attachment portion 132 is adjacent to (and/or abuts) the distal abutment portion 114, though, other locations are contemplated within the scope of the present disclosure.

As best seen in FIGS. 3, 5 and 6, in certain embodiments, the connector 100 can include wireless electrical circuitry such as Bluetooth or WiFi based communication, which can be established between the connector 100 and the charger 200 to identify the pressure sensing catheter 10 connected to the connector 100.

Referring back to FIG. 1, embodiments of the present disclosure include a charger 200 for charging the one or more balloons 40 of the catheter 10 connected (e.g., via the connector 100) to the charger 200. The charger 200 comprises a charger housing 202 that encloses one or more charging ports 204 thereof. In optional embodiments, the charger 200 may, in some cases, be referred to as a patient interface module 200. The patient interface module 200 may be positionable on or near a patient during a measurement procedure. The patient interface module 200 may be integrated into another medical device, a lanyard, or the like. The patient interface module 200 may include one or more of components such as the charger housing, charging ports 204, covers, pressure transducers 222, electrical connectors, electrical circuitry (advantageously provided as a circuit board) for performing processing, data storage, wired or wireless communications and associated electrical accessories.

Appreciably, the charger housing 202 can include an interface for permitting one or more external connections. The electrical connection interfaces can permit detachable coupling of the patient interface module 200 to one or more cable assemblies, in turn coupling (either by a wired connection or wirelessly) to a processor (for instance, application specific integrated circuits (ASICs), microcontrollers, microprocessors, field-programmable gate arrays (FPGAs), or any other appropriate structure capable of receiving and processing data, as well as, circuitry distributed across a network to receive and process data and control system operation as described herein from a remote location). In one aspect where the cable assembly comprises a wired reusable assembly, the reusable assembly can have, at its proximal end, an electrical connector configured to be connected to a processor and monitor. In such embodiments, a data/power cable of a reusable interface cable can operatively connect electrical components of the patient interface module 200 to transmit pressure measurements to the processor.

According to advantageous embodiments, the patient interface module 200 may be compact and light-weight so as to remain supported on the patient. For example, the patient interface module 200 can have a length of between about 70 millimeters and about 100 millimeters, a width of is between about 40 millimeters and about 70 millimeters, and a height of between about 10 millimeters and about 30 millimeters. In one embodiment, the patient interface module 200 can have a length of about 75 millimeters, a width of is between about 58 millimeters, and a height of 26 millimeters. In advantageous aspects, the patient interface module 200 can have a weight of between about 50 grams and about 80 grams. In one example, the patient interface module 200 can have a weight of between about 70 grams. However, the dimensions and other numeric values and/or ranges disclosed herein should not be construed as limiting.

As seen in FIG. 1, the charger 200 includes one or more charging ports 204. In the illustrated embodiment, the charging ports 204 are recessed from an upper portion of the charger housing 202. Alternatively, other locations of the charging ports 204 are also contemplated within the scope of the present disclosure. While four ports are illustrated, additional or fewer ports are contemplated within the scope of the disclosure.

Figure 7:
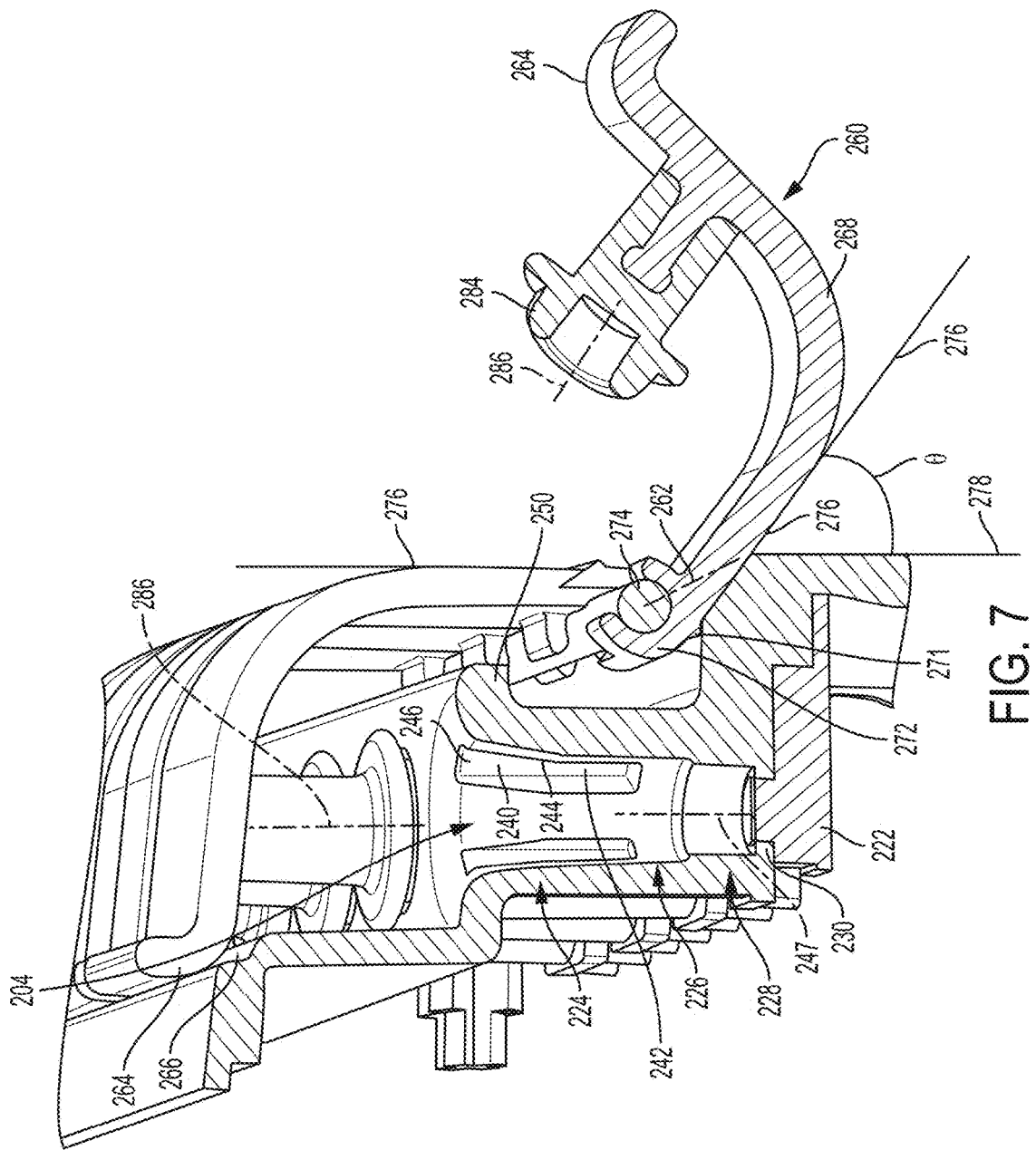
FIG. 7 is a partial sectional view of the charger of FIG. 1 according to an embodiment shown without a connector engaged thereto.
Figure 8:
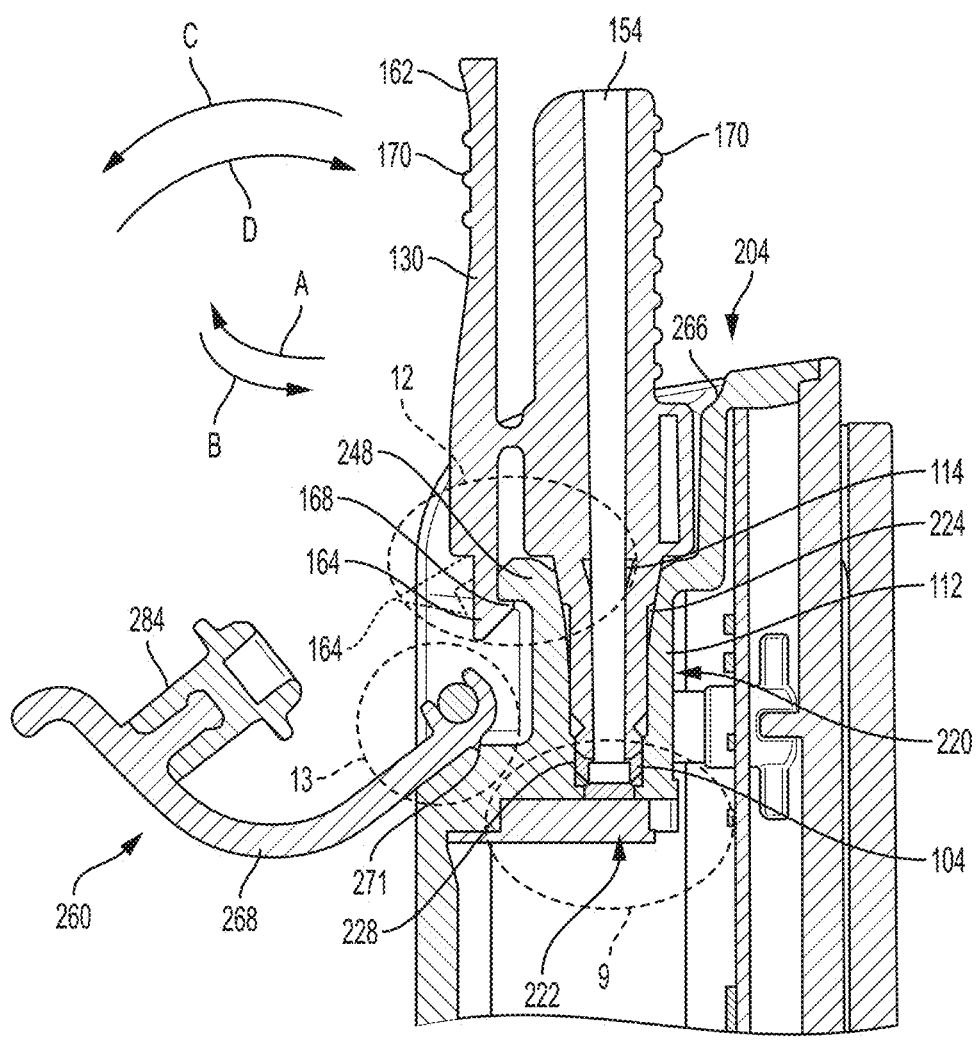
FIG. 8 is a partial section view of the charger of FIG. 1 shown with a connector engaged thereto (but without a catheter)

FIGS. 7 and 8 illustrate a sectional view of a charging port 204 without and with a connector 100 engaged with the charging port 204 respectively according to an embodiment. As seen therein, the charging port 204 can have a second engagement portion 220 for engaging with the first engagement portion 102 of the connector 100.

At least one of the first engagement portions 102 and the second engagement portions 220 can have the pressure transmission medium therewithin. Accordingly, in some such embodiments, when the first engagement portion 102 and the second engagement portion 220 engage, at least portions of the second engagement portion 220 can become fluidly coupled to the monitor lumen 30 (via the catheter 10 inserted into the lumen 154 running through the body of the connector 100). The fluid coupling of portions of the second engagement portion 220 can displace the pressure transmission medium present in either of the first engagement portion 102 or the second engagement portion 220, thereby charging the one or more balloons 40. In an embodiment, the pressure transmission medium present in a portion of the charging port 204 is used for charging the balloons.

Figure 9:
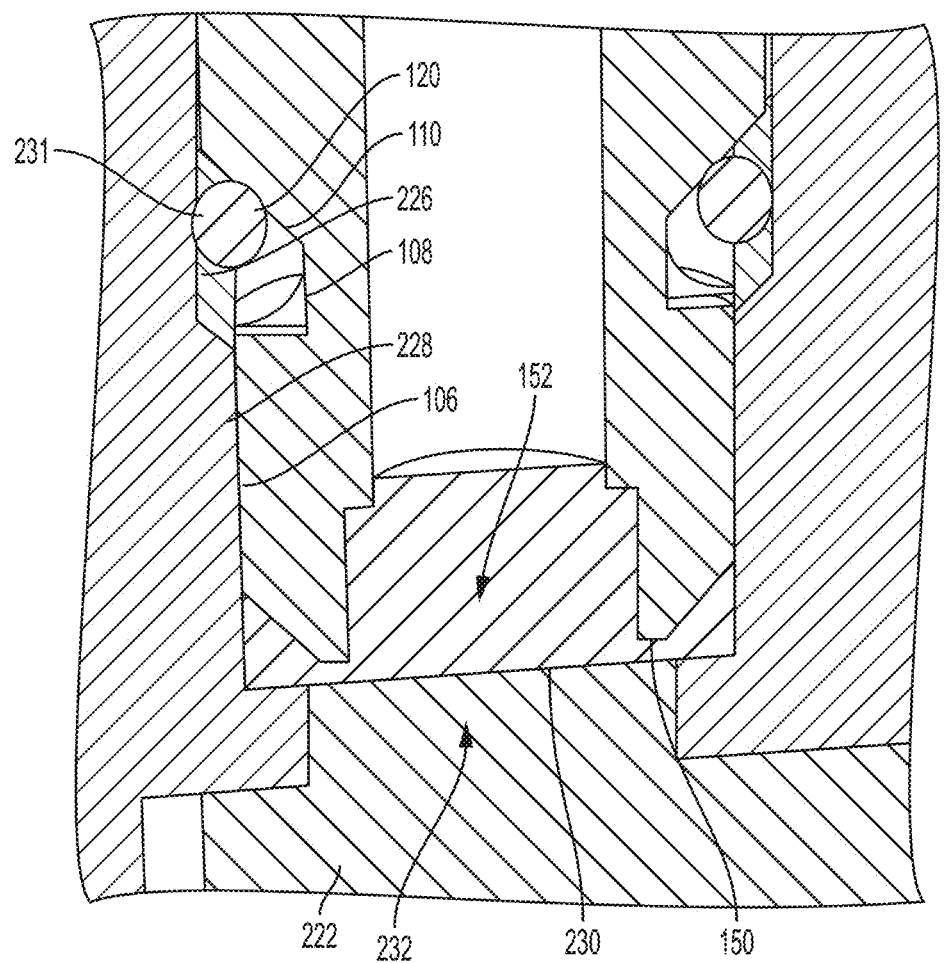
FIG. 9 is an enlarged perspective view of the portion 9 shown in FIG. 8.

FIGS. 8 and 9 illustrate a sectional view of the patient interface module 200. As seen from FIGS. 8 and 9, the patient interface module 200 can include a plurality of pressure transducers 222 for measuring anatomical pressure. In the illustrated embodiment, each charging port 204 has a corresponding pressure transducer 222. In some embodiments, the pressure transducer 222 can be a diaphragm, piezoelectric transducer and the like and can generate electrical signals in response to a change in pressure. When the connector 100 is engaged with the charging port 204, the pressure transducer 222 can interface (e.g., be in fluid communication) with the fluid column of the connector 100, and that of the catheter 10 to detect changes in anatomical pressure (e.g., urodynamic pressure) acting on the balloon 40.

As described previously, electrical connection interfaces can electrically connect (e.g., via one or more electrical cables and/or the electrical circuitry configured as a circuit board) the pressure transducer 222 to an external computer, a processor and/or a monitor. In one aspect, a wired connection can be established by an electrical cable connected to a processor and monitor. In such embodiments, the pressure transducer 222 can be coupled to a data/power cable to transmit pressure measurements to the processor and/or provide power to the pressure transducer 222.

Referring back to FIGS. 7 and 8 that illustrate a sectional view of a charging port 204, the second engagement portion 220 can have a distal end portion 224, a connecting portion 226 and a proximal end portion 228. The connecting portion 226 can extend between the distal end portion 224 and the proximal end portion 228. The proximal end portion 228 of the charging port 204 can receive the proximal abutment portion 106 and/or the proximal end portion 104 of the connector 100. The distal end portion 224 can receive the distal abutment portion 114 and portions of the connecting portion 112 of the first engagement portion 102 of the connector 100, while the connecting portion 226 of the charging port 204 can receive the remainder of the connecting portion 112 of the first engagement portion 102 that extends beyond the distal end portion 224 of the charging port 204.

The distal end portion 224, the connecting portion 226 and/or proximal end portion 228 of the charging port 204 can be of variable cross-sectional area so as to matingly engage with the distal abutment portion 114, connecting portion 112, proximal end portion 104 and/or proximal abutment portion 106 of the connector 100. When mating engagement is established, for instance, as seen in FIG. 8, an outer surface of at least portions of the connector 100 can abut an interior surface of at least portions of the charger 200.

Figure 10B:
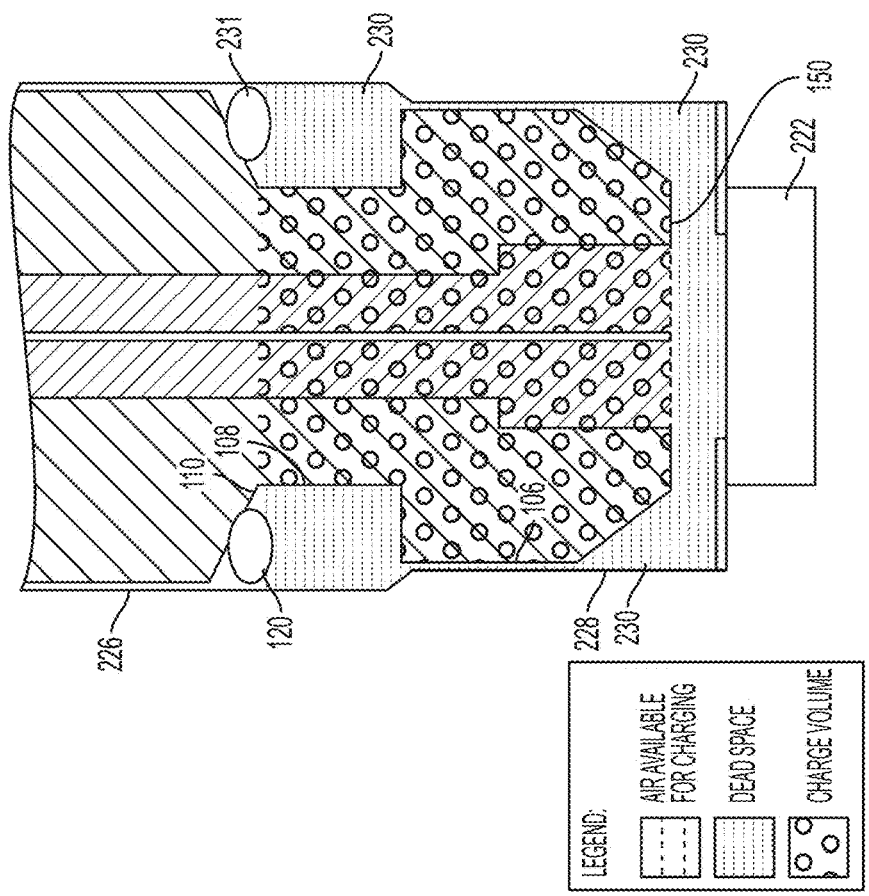
FIGS. 10A and 10B are schematics illustrating volume of pressure transmission medium available for charging the balloons and dead space, respectively.
Figure 10A:
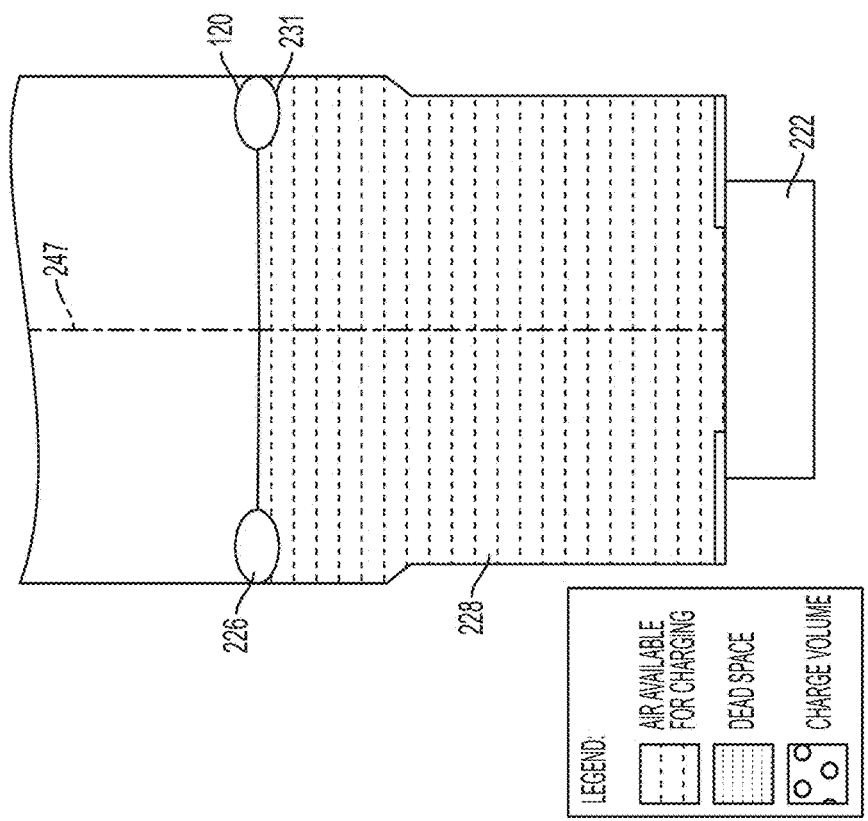

In advantageous aspects, the connector 100 may be connected to the charging port 204 such that a proximal end portion 104 of the connector 100 may be in close proximity to the pressure transducer 222. In an embodiment, as seen in FIGS. 9 and 10A, 10B, the pressure transducer 222 can have a proximal end surface 230, near or inserted against an aperture 232 of the charging port 204. The connector 100, in turn, can also have a proximal end surface 150 that surrounds a proximal opening 152 of the connector lumen 154. When correctly inserted (as will be described further below), the proximal end surface 150 of the connector 100 can be in close proximity to the proximal end surface 230 of the pressure transducer 222.

As illustrated in FIGS. 9, 10A, 10B, the proximal end surface 150 of the connector 100 can be spaced apart from the proximal end surface 230 of the pressure transducer 222 by at least portions of the dead space. When inserted properly (as will be described further below), the proximal opening 152 of the connector lumen 154 can directly face the pressure transducer 222, and thereby be directly in fluid communication with the pressure transducer 222.

In certain embodiments, a quantity of the pressure transmission medium may be present in a portion of the charging port 204 even after proper insertion of the connector 100 into the charging port 204. This may equal the volume of pressure transmission medium present in the portion of the charging port 204 that is available for displacement prior to insertion of the connector 100, but has not been used for charging the balloons 40 after insertion of the connector 100. This quantity of the pressure transmission medium may be referred to as "dead space," and may, in some embodiments, lead to damping of pressure fluctuations, as a result of compression of the pressure signals transmitted from the balloons 40. If, for instance, the dead space is present in direct vicinity of the pressure transducer 222, responsiveness of the pressure transducer 222 may be reduced.

In certain embodiments, dead space may refer to a volume of pressure transmission medium that does not move during charging. Accordingly, in some such embodiments, the volume of pressure transmission medium that does not move during charging may generally equal the volume of pressure transmission medium present in the portion of the charging port 204 that is available for displacement prior to insertion of the connector 100, but has not been used for charging the balloons 40 after insertion of the connector 100. Alternatively, in other embodiments, the volume of pressure transmission medium that does not move during charging may differ from the volume of pressure transmission medium present in the portion of the charging port 204 that is available for displacement prior to insertion of the connector 100, but has not been used for charging the balloons 40 after insertion of the connector 100. The difference may be about equal to a volume of pressure transmission medium present in the lumen 154 at the time of engagement between the connector and the charging port 204.

In some advantageous aspects of the present disclosure, dead space may be minimized by configuring connections between the connector 100 and the charging port 204 to have the pressure transducer 222 be in direct fluid communication with connector 100. Such direct fluid communication between the proximal opening 152 of the connector 100 and the pressure transducer 222 (such as those disclosed above) may reduce the dead space to improve measurement responsiveness.

As seen in FIGS. 10A and 10B, the portion of the charging port 204 may correspond to the portion that extends between a proximal end surface 230 of pressure transducer 222 (inserted into or placed near aperture 232) and a point 231 on the connecting portion 226 where the resilient seal contacts the second engagement portion 220 after proper insertion of the connector 100 in the charging port 204. A first volume of pressure transmission medium available in this portion may be referred to as a charge volume and may be displaced into the lumen 154 when sealing engagement between the first engagement portion and the second engagement portion is established. A second volume of the pressure transmission medium may be present in the same portion as the first volume (corresponding to an area that, upon engagement between the first and second engagement portions, would be sealed by the resilient seal 120) prior to insertion may be referred to as the total volume and can be illustrated by shaded area in FIG. 10A. The first volume may generally be less than (or preferably equal to) the second volume. Appreciably, the total volume may not include the entire volume of the charging port 204, but merely just portions thereof. The volume of pressure transmission medium present in this portion that has not been displaced may be referred to as "dead space," as illustrated by the shaded portion in FIG. 10B, and may be equal to the difference between the first volume and the second volume. The dead space, as shown in FIG. 10B, may have portions that annularly surround the exterior surface of the proximal end portion 106, seal groove 108 and at least portions of the ramp portion 108 of the connector 100. The dead space may also include portions that separate the proximal end surface 150 of the connector 100 from a proximal end surface 230 of the pressure transducer 222. Appreciably, physical coupling of the connector 100 and the charging port 204 to position the pressure transducer 222 in close proximity with the connector 100's proximal opening 152 may result in desirable ratios of dead space to charge volume (for instance, less than about 40%).

In an example embodiment, the total volume, as defined above, may be about 35 microliters, the charge volume, as defined above, may be about 30 microliters, and the dead space, as defined above, may be about 5 microliters. Accordingly, a ratio of dead space to charge volume can be less than about 1:2.5, or less than about 40%. In one embodiment, the ratio of dead space to charge volume can be about 1:6, or about 17%. Such embodiments may improve measurement responsiveness.

When direct fluid communication is established between the pressure transducer 222 and the proximal opening 152, the pressure transducer 222 and the proximal opening 152 may still be separated by the dead space having a quantity of pressure transmission medium, such that pressure variations (e.g., from the balloons 40) may be communicated via the dead space to the pressure transducer 222. Appreciably, disclosed embodiments minimize the dead space by suitably designing the geometry of the connector 100 and the charging port 204 such that pressure measurements of improved accuracies are obtainable.

In advantageous aspects, most (e.g., greater than about 60%, for example, about 83%), if not nearly all the pressure transmission medium present in the charging port 204 prior to the insertion of the connector 100 may get displaced into the lumen of the connector 100, and be transmitted to the one or more balloons 40. Accordingly, in optional embodiments, the total volume of fluid in the charging port 204 prior to insertion may be approximately equal to the charge volume (or displaced volume of the pressure transmission medium).

In some such embodiments, the dead space can enclose a volume of between about 1 microliters and about 10 microliters of pressure transmission medium (e.g., about 5 microliters), when a charge volume of pressure transmission medium that charges the balloons 40 is about 30 microliters.

According to certain embodiments, coupling of the connector 100 and the charging port 204 so as to have the proximal opening 152 in close proximity to the pressure transducer 222 may result in improved frequency response of the catheter 10. In advantageous embodiments, the pressure transducer 222 to measure pressure at a rate so as to capture anatomical pressure variations having a characteristic frequency of between about 1 Hz and about 50 Hz.

In additional or alternative aspects, the proximity of the pressure transducer 222 and the proximal opening 152 of each charging port 204 can also permit the patient interface module to be substantially fluid-tight. For example, the pressure transducer 222 can fluidly isolate the charging port 204 from an interior of the patient interface module, such that fluid entering into the charging port is prevented from entering further into the interior of the patient interface module, such that electrical components (e.g., electrical connection interfaces, electrical circuitry provided in the form of a circuit board, EMG connectors, cables, sockets, pins, etc.) housed within the interior of the patient interface module may be protected from fluid ingression.

Figure 11:
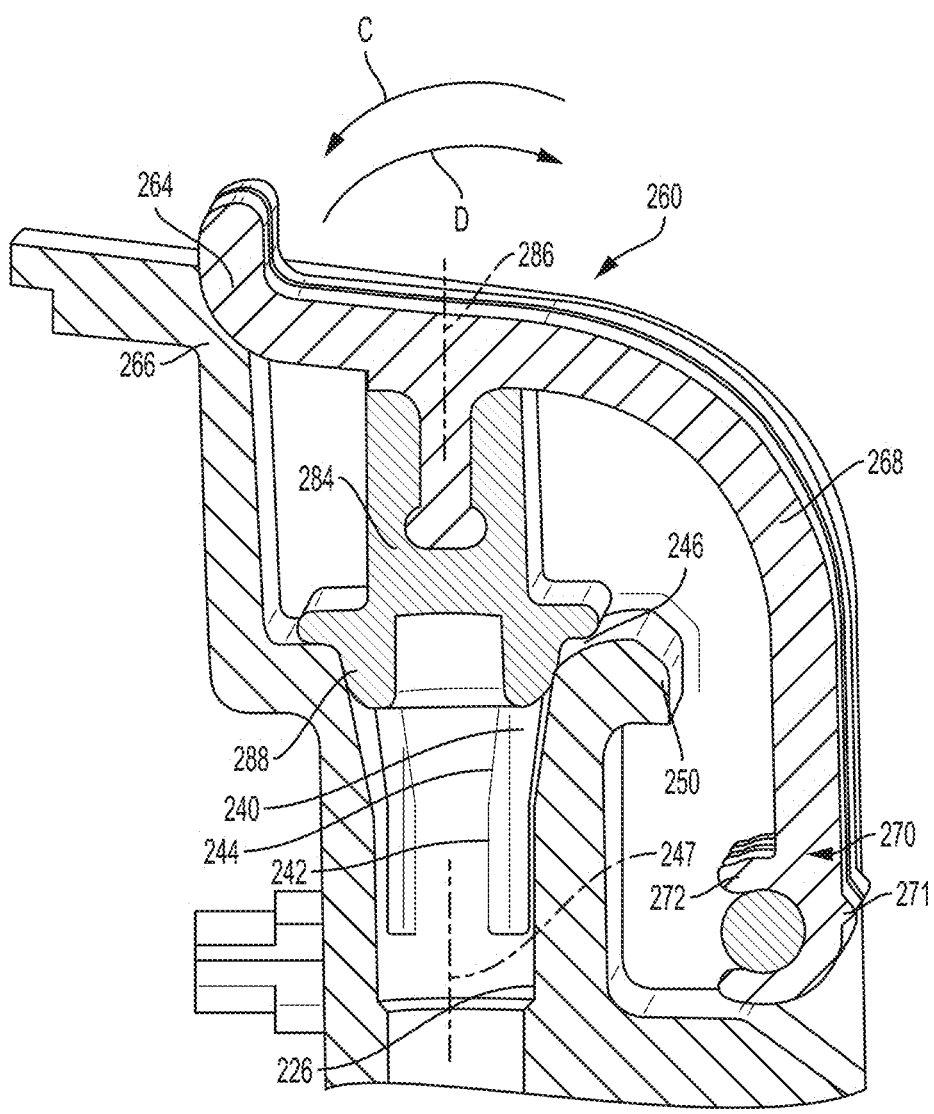
FIG. 11 is a partial section view of the charger of FIG. 1 shown with the cover in the closed position.

With reference to FIG. 11, according to exemplary embodiments, the second engagement portion 220 includes a plurality of flutes 240 defined on the interior surface. The flutes 240 can have a generally tapering shape relative to a central (e.g., longitudinal) axis of the second engagement portion 220. In the illustrated embodiment, the flutes 240 are formed as recesses on the interior surface. The recesses may have a first portion 242, and a second portion 244. The second portion 244 may extend from an outer edge 246 of the charging port 204 and till the first portion 242 of the recess. Appreciably, the outer edge 246 may either be the outermost edge of the charging port 204, or may define another edge generally near the outermost edge of the charging port 204. The second portion 244 (and/or the interior surface of the charging port 204) may taper gradually inwardly toward the central axis 247 when viewed from the outer edge 246 of the charging port 204. As illustrated, in some such cases, the flutes 240 may be defined on interior surface of the second engagement portion 220 at regular intervals.

As illustrated, the flutes 240 extend for a length that corresponds to a length of the distal end portion 224 of the charger 200. In some advantageous embodiments, the second portion 244 of the flutes 240 can extend an entire length of the distal end portion 224 of the charger 200, while the first portion 242 of the flutes 240 can extend over at least for a partial length of the connecting portion of the charger 200. While four flutes 240 per charging ports 204 are shown, additional or fewer flutes 240 can be contemplated. In certain advantageous embodiments, the flutes 240 may facilitate a more precise control of the charge volumes as will be described further below.

Referring back to exemplary embodiments such as those illustrated in FIG. 8, the distal abutment portion 114 of the connector 100 can also gradually taper, which can match the taper angle of the second portion 244 of the flutes 240. Further, the connecting portion 112 of the connector 100 can be generally cylindrical in some embodiments, as seen in FIGS. 3 and 4. Referring again to FIGS. 8 and 9, when the connector 100 is received within the charging port 204, the distal abutment portion 114 of the connector 100 can engage with the second portion 244 of the flute proximal to the outer edge 246 of the charging port 204. The connecting portion 112 can also abut the first portion 242 of the flutes 240. Some such configurations, together with other features disclosed herein can permit charging the balloons 40 correctly (e.g., not undercharging or overcharging).

Referring again to FIGS. 3-6, in some embodiments, the connector 100 includes a handle 130 attached to a body portion thereof. The handle 130 has a first end 160 and a second end 162. The second end 162 can be opposite to the first end 160, and distal relative to the charging port 204. The first end 160 can have a tab 164. The tab 164 can be flexible relative to at least portions of the handle 130. The tab 164 can, in one embodiment, have a thickness less than a thickness of the handle 130 at locations other than the first end 160. Accordingly, the tab 164 may be flexible relative to portions of the handle 130 other than the first end 160.

In some embodiments, when the second end 162 of the handle 130 is depressed (e.g., by applying a force or a torque), the force or torque can be transmitted to the first end 160, in turn flexing the tab 164 relative to the body of the connector 100 (e.g., toward or away from the longitudinal axis 169 of the connector 100). The tab 164 can, as will be described below, in some embodiments, provide a tactile, audible, haptic or other types of feedback to the operator to indicate that proper engagement between the connector 100 and the charging port 204 has been established and reduce the risk of undercharging the balloons.

Referring again to FIG. 3-6, the tab 164 can have an angled surface 166 forming a non-zero angle with the longitudinal axis 169 of the connector 100. The angled surface 166 can abut an end surface 168 of the tab 164. In the illustrated embodiment, the end surface 168 is also non-parallel to the longitudinal axis 169 of the connector 100. The end surface 168 can, in some embodiments, be perpendicular to the longitudinal axis 169 of the connector 100. Accordingly, the tab 164 can have a triangular cross-section at the end as seen in the exemplary embodiment of FIG. 3-6. However, other cross-sectional profiles (rectangular, radiused, rounded, etc.) that would provide a similar functionality are contemplated within the scope of the present disclosure.

Figure 12:
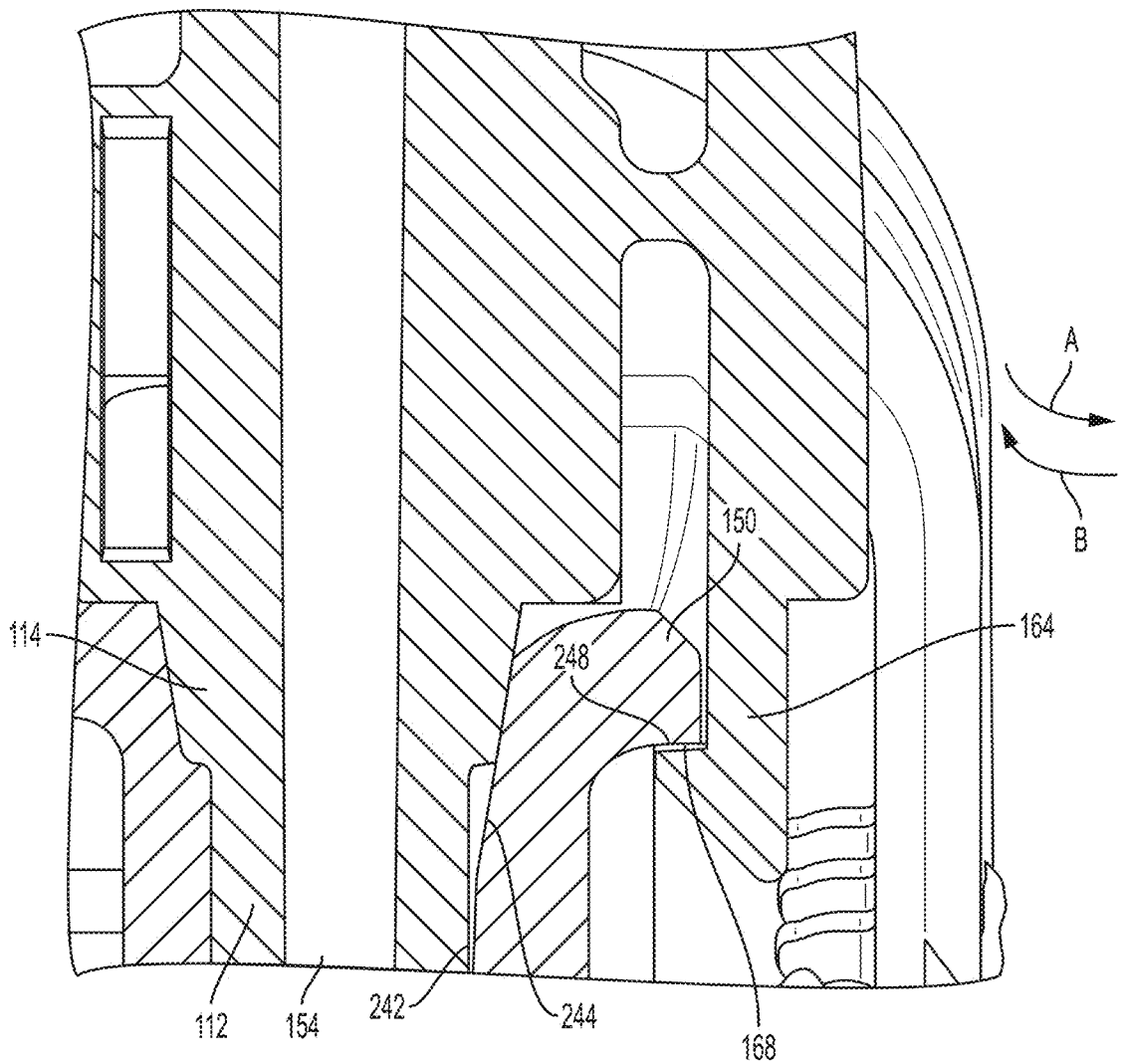
FIG. 12 is an enlarged view of the portion 12 shown in FIG. 8.

Referring now to FIG. 12, the charger 200 can have an engagement surface 248 proximal to the outer edge 246 of the charging port 204. In the illustrated example, the charger 200 has a lip 250 adjacent to the outer edge 246 of the charging port 204. The lip 250 can protrude outward away from the central axis 247 of the charging port 204. The engagement surface 248 of the charger 200 can be provided on a side opposite to the outer edge 246 of the charging port 204. In the illustrated embodiment, the engagement surface 248 can be defined on an underside of the lip 250. During insertion, portions of the lip 250 may interfere with the tab 164 and push (e.g., along direction "A") the tab 164 away from the lip 250 (e.g., as shown by dashed lines). Once the connector 100 is inserted such that the tab 164 no longer interferes with the lip 250, the tab 164 may be move back (e.g., along direction "B") to engage with the engagement surface 248 of the charger 200.

As seen in FIG. 12, the end surface 168 of the tab 164 can engage with the engagement surface 248 of the charger 200 when the distal abutment portion 114 engages with the portion 244 of the flutes 240, and the connecting portion 112 engages with the portion 242 of the flutes 240. Appreciably, further pushing of the connector 100 into the charger 200 may be avoided by the engagement between the end surface 168 and the engagement surface 248, as well as by the abutment of the distal abutment portion 114 against the portion 244, and the connecting portion 112 against the portion 242. The abutment of such surfaces and portions may provide an audible "click" or "snap," and/or may provide tactile feedback in the form of two engaging/mating surfaces. This may cause the operator to realize that adequate engagement has been established between the connector 100 and the charging port 204, and the operator may not inadvertently push the connector 100 further into the charger 200, thereby reducing the risk of overcharging the balloons 40.

In advantageous aspects, the connector 100 can be inserted in any rotational orientation about the longitudinal axis 169 of the connector 100. In an embodiment, the lip 250 extends around a perimeter of the charger housing 202. Accordingly, there may be more than one rotational position of the connector 100 (about the longitudinal axis 169) where engagement between the end surface 168 of the tab 164 and the engagement surface 248 of the charger housing 202 can be made possible. While in FIG. 8, the sectional view illustrates the lip 250 (and the engagement surface 248) extending on the left side of the drawing, in alternative embodiments, the lip 250 (and the engagement surface 248) can extend on the right side. Other positions of the lip 250 and the engagement surface 248 are also possible. Alternatively, in other embodiments, the connector 100 can be "keyed" so as to orient the connector 100 in an appropriate rotational orientation. The connector 100, for instance, can include an alignment element (e.g., a protrusion 271, a slot, or the like) to help orient the connector 100 such that the tab 164 faces the lip 250 during insertion of the connector 100 into the charging port 204.

In certain optional embodiments, referring back to FIGS. 3-6, the second end 162 of the handle 130 comprises a thumb grip portion 170. The thumb grip portion 170 can be grasped by an operator's thumb. The thumb grip portion 170 can have a plurality of ribs to permit frictional engagement with the operator's thumb to ergonomically guide the user's thumb to apply sufficient the disengagement torque on the first end 160 to release the engagement between the first end 160 and the engagement surface 248 of the charger 200. This may advantageously reduce unwanted stress on the operator's thumb, (for instance, the musculature for thumb opposition, such as the adductor, flexor and abductor pollicis brevis) and wrist.

In further optional embodiments, the connector 100 may also include a plurality of finger grips 172 provided on a portion of the connector 100's body. The finger grips 172 can be oriented in an opposite direction to the thumb grip portion 170. The finger grip portion can be proximal to the second end 162 of the handle 130.

During insertion, referring to FIGS. 8 and 12 the operator may place their fingers on the finger grip portion and push the connector 100 toward a charging port 204. The end surface 168 of the tab 164 may encounter a surface (e.g., a lateral surface) of the lip 250, and by virtue of its flexibility, may be pushed (e.g., radially outward) relative to the longitudinal axis 169 of the connector 100. Once the end surface 168 stops encountering interference from one or more surfaces of the lip 250, it may move (e.g., by virtue of its flexibility) radially inwardly toward the longitudinal axis 169 and abut the engagement surface 248 of the charger 200. At this instance, the operator may receive (audible or tactile) feedback indicative of the engagement between the engagement surface 248 and end surface 168 and/or between the distal abutment portion 114 and/or second portion 244, and/or between the connecting portion 112 and the first portion 242, the operator may stop pushing the connector 100 further into the charging port 204.

To disengage the connector 100, the operator may apply a disengagement torque on the second end 162. For example, the operator may place their thumb on the thumb grip portion 170 of the handle 130 and apply a disengagement torque, which may be transmitted to the first end 160. This can cause the tab 164 to move away from the lip 250, for instance, along direction "A". The operator may remove (e.g., pull) the connector 100 from the charging port 204 by placing their fingers on the finger grip portion. Advantageously, the finger grip portion may provide added friction between the user's fingers and the connector 100, thereby reducing the risk of inadvertently dropping the connector 100.

Referring again to FIG. 1, in aspects of the disclosure, each charging port 204 can include a cover 260 to keep the charging ports 204 covered when not in use. The cover 260 can be movable between an open position and a closed position. In the closed position, the cover 260 fluidly seals the second engagement portion 220 to reduce the risk of ingression of dust, fluids and the like into the charging port 204 when not in use. The cover 260 can be moved to the open position to permit engagement of the connector 100 with the charging port 204. In FIG. 1, one of the covers is shown in the open position, while the remaining covers are shown in the closed position.

As illustrated in FIG. 1, according to an embodiment, the cover 260 rotates about a rotational axis 262 between the open and closed position. The rotational axis 262 can be generally non-parallel (e.g., perpendicular) to the central axis 247 of the charging port 204. Other types of movement (such as sliding motion between the open and closed position) are also contemplated within the scope of the present disclosure.

In aspects of the disclosure, the cover 260 can be removably coupled with each charging port 204. In one embodiment, the cover 260 can engage with the charging port 204 by a snap-fit connection. Additional connections such as frictional connection, or one or more fasteners and the like are contemplated. According to exemplary embodiments, the cover 260 may terminate in a lip 264, portions of which can abut a corresponding angular surface 266 on the charger housing 202, having a shape complementary as the portion of the lip. Prior to insertion of a connector 100, the operator may grasp the lip 264 and rotate the cover 260 about its rotational axis 262 to move the cover 260 to the open position. After use, the operator may grasp the lip 264 again, and move the cover 260 to the closed position.

FIG. 11 illustrates a partial sectional view of the charger 200 according to an embodiment. The cover 260 can have a cover base 268. The cover base 268 can be detachably coupled to the charger housing 202 in an embodiment. In the illustrated embodiment, the coupling between the cover base 268 and the charger housing 202 can be a pivotal coupling which can permit the cover 260 to rotate between the open position and the closed position.

Referring to an enlarged side view of FIG. 12, in an embodiment, the cover base 268 has a tip portion 270. The tip portion 270 terminates in a receiving portion 272 that can be sized and shaped to receive a pivot pin 274. For example, the receiving portion 272 can be C-shaped, as illustrated, though, other shapes are contemplated. The pivot pin 274 can be centered on the rotational axis 262 of the cover 260. The pivot pin 274 can frictionally engage with the C-shaped receiving portion 272 and slide on an outer surface of the pivot pin 274 when the cover 260 is moved between the open position and the closed position. Appreciably, a single pivot pin 274 can frictionally engage with more than one cover 260, though, alternatively, separate pivot pins can be used with separate covers, if desired.

In certain embodiments with reference to FIGS. 7 and 8, the geometry of the cover 260 can permit the cover 260 to be in a position so as to not interfere with the insertion of the connector 100 into the charging port 204. In one example, the cover base 268 can have a generally planar surface 276. The charger housing 202 can also have a generally planar surface 278. The geometry of the cover 260 can be such that the generally planar surface 276 of the cover base 268 can be generally coplanar with the generally planar surface 278 of the charger housing 202 when the cover 260 is in the closed position. Further, the generally planar surface 276 of the cover base 268 can be generally non-coplanar with the generally planar surface 278 of the charger housing 202 when the cover 260 is in the open position. The generally planar surface 276 of the cover base 268 can, in such cases, form an angle θ of between about 30 degrees and about 70 degrees with the generally planar surface 278 of the charger housing 202 when the cover 260 is in the open position. Such geometric configurations and angular relationships between the cover 260 and the charger housing 202 may permit the cover 260 to remain at a position so as to not interfere with the insertion of the connector 100 into the charging port 204.

Figure 13:
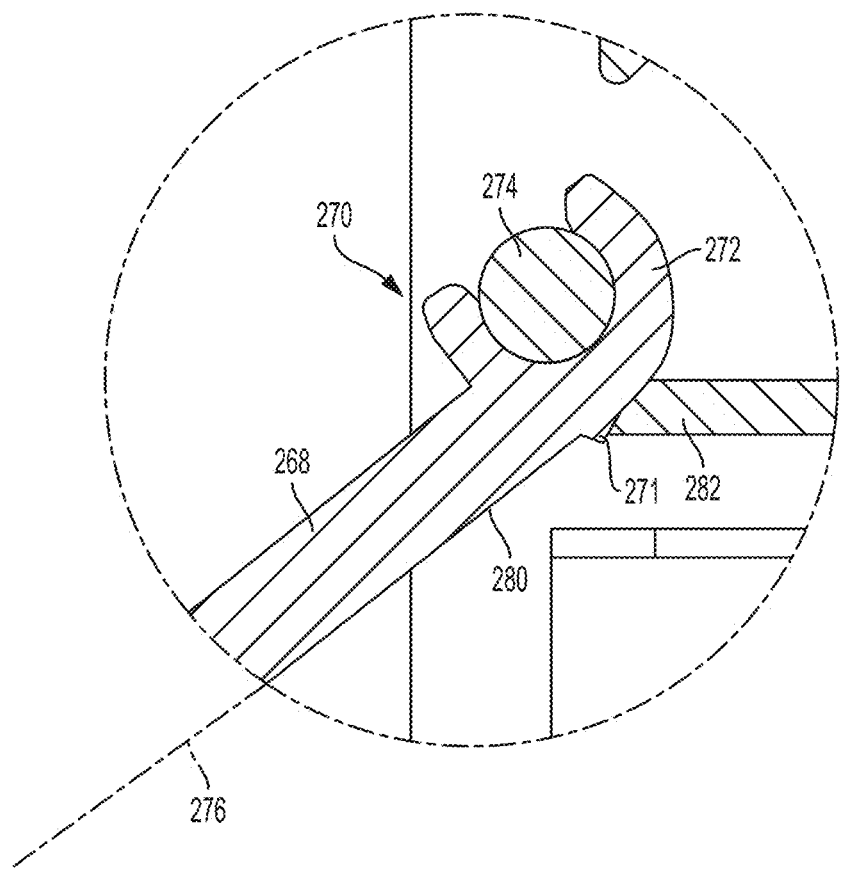
FIG. 13 is an enlarged view of the portion 13 shown in FIG. 8.

With reference to FIGS. 11-13, in certain embodiments, the cover 260 can be maintained in an open position unless a manual force is applied thereon to move the cover 260. Further, advantageously, cooperative structures on the cover 260 and the charger 200 may limit further rotation of the cover 260 when in the open position. FIG. 13 illustrates one such cooperative structure. As seen in FIG. 12, the charger housing 202 comprising a charger housing angled surface 280. The charger housing angled surface 280 can form an angle of between about 20 degrees and about 80 degrees with the generally planar surface 278 of the charger housing 202 when the cover 260 is in the open position. When the cover 260 is in the open position, the cover base 268 can rest against the charger housing angled surface 280 so as to maintain the cover 260 in the open position. Advantageously, this may restrict further rotation of the cover base 268 in the direction "C". In some such embodiments, the cover 260 may remain open by self-weight/gravity when the cover 260 is rotated beyond a first rotational position. The first rotational position can be a position generally half-way between the closed position and the position at which the cover 260 rests against the charger housing angled surface 280.

In optional advantageous embodiments, cooperative structures on the cover 260 and the charger 200 may reduce and/or prevent inadvertent closure of the cover 260 during insertion of the connector 100 or use. As seen in FIG. 12, the cover base 268 terminates in the tip portion 270 opposite to the lip 264 of the cover 260. The tip portion 270 can be near the pivotal coupling between the cover base 268 and the pivot pin 274. The tip portion 270 can have a protrusion 271 for engaging with a cooperative structure of the charger housing 202 to restrict movement of the cover 260 in the direction "D" (opposite to the direction "C"). The protrusion 271, in the illustrated embodiment is V-shaped, and extends outwardly from the receiving portion 272.

In one example, the charger housing 202 has a charger housing end surface 282. The charger housing end surface 282 can abut and/or form an angle with the charger housing angled surface 280. Such an angular relationship can permit the cover base 268 to rest against the charger housing angled surface 280 while the protrusion 271 rests against the charger housing end surface 282. When the protrusion 271 rests against the charger housing end surface 282, the cover 260 may not be inadvertently closed until an operator grasps the lip 264 and applies a force/torque to rotate the cover 260 and move the protrusion 271 away from the charger housing end surface 282. Accordingly, such positional and/or angular relationship can advantageously inhibit inadvertent closure of the cover 260 (e.g., during insertion of the connector 100 or use).

In certain aspects of the disclosure, the covers can be held securely in the closed position to reduce risk of ingression of dust or moisture. In one such embodiment, the cover 260 may include a cover plug 284 extending from the cover base 268. The cover plug 284 may be pointed away from the cover base 268. In the illustrated embodiment, cover plug 284 has a cover plug center axis 286, which is generally parallel to the generally planar surface 276 of the cover base 268. The cover plug 284 can engage with the second engagement portion 220 to maintain the cover 260 in the closed position. The cover plug 284 can, in some such embodiments, fluidly seal the second engagement portion 220.

According to some embodiments, the cover plug 284 has an interference fit with the second engagement portion 220 to maintain the cover 260 is in the closed position. FIG. 11 illustrates one such example. The cover plug 284 comprises a tapered portion 288. In some embodiments, a maximum diameter of the tapered portion 288 maybe greater than a maximum diameter of a charging port 204. However, the cover plug 284 may be resilient relative to the charging port 204 which may permit the cover plug 284 to be pressed into at least portions of the charging port 204. In the illustrated embodiment, the cover plug 284 abuts the distal end portion 224 of the charging port 204.

The cover plug 284 can have a resilient material to permit desired degree of interference between the charging port 204 and the cover plug 284, as well as to cushion the charging port 204 in the event of damage (e.g., such as when the charger 200 is inadvertently dropped). In some examples, the resilient material can be a material that has a Shore A durometer hardness of between about 50 and about 95. In some preferred embodiments, the material can have Shore A durometer hardness of about 70-95. In optional embodiments, the cover plug 284 can have at least portions thereof made of materials such as elastomer, thermoplastics, rubber, silicon and the like.

Embodiments disclosed herein provide a number of advantages. According to some embodiments, the charger 200 can be configured to be light-weight. The connector 100 can ensure a secure connection with the charger 200 and permit precise control of the charge volume. Further, accuracy of pressure readings can be improved by minimizing the dead space, and improving the frequency response of pressure measurements.

Various examples have been described. These and other examples are within the scope of the following claims.

The invention claimed is:

1. A charger for charging one or more balloons of a pressure sensing catheter with a pressure transmission medium, the charger comprising:
   a charger housing;
   a charging port configured to receive a portion of a proximal section of a pressure sensing catheter, the charging port including:
   a central axis,
   a first end,
   a second end opposite to the first end in a first direction parallel to the central axis,
   a connecting charging port portion located between the first end and the second end of the charging port, the connecting charging port portion forming at least a portion of a length of an interior surface of the charging port, the connecting charging port portion tapering inward toward the central axis along the length of the interior surface, the connecting charging port portion configured to contact a seal on the proximal section of the pressure sensing catheter as the proximal section of the pressure sensing catheter is received in the charging port,
   a flute extending between a first end and a second end of the flute, the second end of the flute being opposite to the first end of the flute in the first direction to define a fluted length, the flute being defined as a recess on the interior surface of the charging port,
   an unfluted length included at the interior surface of the charging port, the unfluted length of the charging port defined between the second end of the flute and the second end of the charging port, and
   the pressure transmission medium therewithin;
   a pressure transducer positioned near the second end of each charging port, the second end being opposite to a direction in which the proximal section of the pressure sensing catheter is to be received in the charging port
   wherein each of the first end and the second end of the flute being spaced apart a length from the second end of the charging port and thereby located away from the pressure transducer, and
   wherein at least some of the unfluted length is included at the connecting charging port portion where the connecting charging port portion tapers inward toward the central axis along the length of the interior surface.

2. The charger of claim 1, wherein the unfluted length being further configured to form a fluid seal with the proximal section of the pressure sensing catheter, the fluid seal of the unfluted length establishing fluid isolation between the flute and the pressure transducer.

3. The charger of claim 1, wherein at least some of the unfluted length and at least some of the fluted length being in the charging port portion such that the connecting charging port portion tapers inward toward the central axis along the length of the interior surface along at least a portion of the fluted length and at least a portion of the unfluted length.

4. The charger of claim 1, wherein the flute comprises a portion tapering inward toward the central axis.

5. The charger of claim 1, wherein the connecting charging port portion is configured to contact the seal on the proximal section of the pressure sensing catheter and continually compress the seal on the proximal section of the pressure sensing catheter via the tapering of the connecting charging port portion as the proximal section of the pressure sensing catheter is moved along the connecting charging port portion toward the second end of the charging port.

6. The charger of claim 1, wherein the charging port comprises two charging port portions located between the first end and the second end of the charging port, the two charging port portions separated by a change in diameter of the charging port forming a transition between the two charging port portions, and wherein the connecting charging port portion forms at least the portion of the length of the interior surface of the charging port at one of the two charging port portions and not at the other of the two charging port portions.

7. A charger for charging one or more balloons of a pressure sensing catheter with a pressure transmission medium, the charger comprising:
   a charger housing;
   a charging port configured to receive a portion of a proximal section of a pressure sensing catheter, the charging port including:
   a central axis,
   a first end,
   a second end opposite to the first end in a first direction parallel to the central axis,
   a connecting charging port portion located between the first end and the second end of the charging port, the connecting charging port portion forming at least a portion of a length of an interior surface of the charging port, the connecting charging port portion tapering inward toward the central axis along the length of the interior surface, the connecting charging port portion configured to contact a seal on the proximal section of the pressure sensing catheter as the proximal section of the pressure sensing catheter is received in the charging port,
   a flute extending between a first end and a second end of the flute, the second end of the flute being opposite to the first end of the flute in the first direction to define a fluted length, the flute being defined as a recess on the interior surface of the charging port,
   an unfluted length included at the interior surface of the charging port, the unfluted length of the charging port defined between the second end of the flute and the second end of the charging port, and
   the pressure transmission medium therewithin;
   a pressure transducer positioned near the second end of each charging port, the second end being opposite to a direction in which the proximal section of the pressure sensing catheter is to be received in the charging port,
   wherein each of the first end and the second end of the flute being spaced apart a length from the second end of the charging port and thereby located away from the pressure transducer, and wherein at least some of the unfluted length and at least some of the fluted length being in the connecting charging port portion, the unfluted length being further configured to form a fluid seal with the proximal section of the pressure sensing catheter, the fluid seal of the unfluted length establishing fluid isolation between the flute and the pressure transducer, and wherein the pressure transmission medium in the flute is displaced away from a lumen of the pressure sensing catheter so as to not charge the one or more balloons, and wherein pressure transmission medium in the unflute length is displaced toward the lumen of the pressure sensing catheter so as to charge the one or more balloons thereby permitting a predetermined volume of the pressure transmission medium to be displaced from the unfluted length of the charging port when the connecting charging port portion of the charging port engages with the proximal section of the pressure sensing catheter.

8. The charger of claim 7, wherein at least some of the unfluted length is included at the connecting charging port portion where the connecting charging port portion tapers inward toward the central axis along the length of the interior surface.

9. The charger of claim 7, wherein the flute comprises a portion tapering inward toward the central axis.

10. The charger of claim 7, wherein the connecting charging port portion is configured to contact the seal on the proximal section of the pressure sensing catheter and continually compress the seal on the proximal section of the pressure sensing catheter via the tapering of the connecting charging port portion as the proximal section of the pressure sensing catheter is moved along the connecting charging port portion toward the second end of the charging port.

11. The charger of claim 7, wherein the charging port comprises two charging port portions located between the first end and the second end of the charging port, the two charging port portions separated by a change in diameter of the charging port forming a transition between the two charging port portions, and wherein the connecting charging port portion forms at least the portion of the length of the interior surface of the charging port at one of the two charging port portions and not at the other of the two charging port portions.

12. A charger for charging one or more balloons of a pressure sensing catheter with a pressure transmission medium, the charger comprising:
a charger housing;
a charging port including:
  a central axis,
  a first end,
  a second end opposite to the first end in a first direction parallel to the central axis,
  a connecting charging port portion located between the first end and the second end of the charging port, the connecting port portion forming at least a portion of a length of an interior surface of the charging port, the connecting charging port portion tapering inward toward the central axis along the length of the interior surface,
  a flute extending between a first end and a second end of the flute, the second end of the flute being opposite to the first end of the flute in the first direction to define a fluted length, the flute being defined as a recess on the interior surface of the charging port,
  unfluted length included at the interior surface of the charging port, the unfluted length of the charging port defined between the second end of the flute and the second end of the charging port, and
  the pressure transmission medium therewithin;
a pressure transducer positioned near the second end of each charging port, the second end being opposite to a direction in which the proximal section of the pressure sensing catheter is to be received in the charging port; and
the pressure sensing catheter having a proximal section with a seal, wherein the charging port is configured to receive at least a portion of the proximal section of the pressure sensing catheter, and wherein the connecting charging port portion is configured to contact and further compress the seal via the tapering of the connecting charging port portion as the proximal section of the pressure sensing catheter is moved along the connecting charging port portion toward the second end of the charging port, wherein each of the first end and the second end of the flute being space apart a length from the second end of the charging port and thereby located away from the pressure transducer wherein at least some of the unfluted length and at least some of the fluted length being in the connecting charging port portion such that the connecting charging port portion tapers inward toward the central axis along the length of the interior surface along at least a portion of the fluted length and at least a portion of the unfluted length.

13. The charger of claim 12, wherein the proximal section of the pressure sensing catheter comprises a connecting portion that engages with the connecting charging port portion as the proximal section of the pressure sensing catheter is moved along the connecting charging port portion toward the second end of the charging port.

14. The charger of claim 13, wherein the proximal section of the pressure sensing catheter further comprises a seal groove and a ramp portion that is positioned between the seal groove and the connecting portion.

15. The charger of claim 14, wherein the seal is positioned in the seal groove prior to the connecting portion engaging the connecting charging port portion, and wherein the seal rides against the ramp portion when the connecting portion engages the connecting charging port portion.

16. The charger of claim 12, wherein the charging port further includes a distal end portion between the first end and the connecting charging port and a proximal end portion between the second end and the connecting charging port.

17. The charger of claim 16, wherein the proximal section of the pressure sensing catheter further comprises a distal abutment portion and a proximal abutment portion, and wherein the distal end portion of the charging port engages the distal abutment portion and the proximal end portion of the charging port engages the proximal abutment portion after the proximal section of the pressure sensing catheter has been moved along the connecting charging port portion toward the second end of the charging port.

18. charger of claim 12, wherein at least some of the unfluted length and at least some of the fluted length being in the connecting charging port portion, the unfluted length being further configured to form a fluid seal with the proximal section of the pressure sensing catheter, the fluid seal of the unfluted length establishing fluid isolation between the flute and the pressure transducer.

19. The charger of claim 18, wherein the pressure transmission medium in the flute is displaced away from a lumen of the pressure sensing catheter so as to not charge the one or more balloons, and wherein pressure transmission medium in the unfluted length is displaced toward the lumen of the pressure sensing catheter so as the charge the one or more balloons thereby permitting a predetermined volume of the pressure transmission medium to be displaced from the unfluted length of the charging port when the connecting charging port portion of the charging port engages with the proximal section of the pressure sensing catheter.

* * * * *